United States Patent
Camus et al.

[11] Patent Number: 6,088,470
[45] Date of Patent: Jul. 11, 2000

[54] METHOD AND APPARATUS FOR REMOVAL OF BRIGHT OR DARK SPOTS BY THE FUSION OF MULTIPLE IMAGES

[75] Inventors: Theodore A. Camus, Mount Laurel, N.J.; Marcus Salganicoff, Philadelphia; Thomas A. Chmielewski, Jr., Langhorne, both of Pa.; Keith James Hanna, Princeton, N.J.

[73] Assignees: Sensar, Inc., Moorestown; Sarnoff Corporation, Princeton, both of N.J.

[21] Appl. No.: 09/013,758

[22] Filed: Jan. 27, 1998

[51] Int. Cl.⁷ .............................. G06T 5/50; G06K 9/36
[52] U.S. Cl. .................... 382/117; 382/275; 351/207; 396/18
[58] Field of Search .................. 382/103, 117, 382/118, 274, 275, 299, 101, 102, 142; 351/206, 207; 396/18, 51, 158; 348/25, 78

[56] References Cited

U.S. PATENT DOCUMENTS

| | | | |
|---|---|---|---|
| 4,516,264 | 5/1985 | Corvari et al. | 382/46 |
| 4,654,583 | 3/1987 | Ninomiya et al. | 324/73 PC |
| 4,661,986 | 4/1987 | Adelson | 382/41 |
| 5,016,282 | 5/1991 | Tomono et al. | 382/2 |
| 5,325,449 | 6/1994 | Burt et al. | 382/56 |
| 5,488,674 | 1/1996 | Burt et al. | 382/284 |
| 5,526,446 | 6/1996 | Adelson et al. | 382/275 |

FOREIGN PATENT DOCUMENTS 0 635 972 A2  1/1995  European Pat. Off. .
0 680 205  11/1995  European Pat. Off. .

OTHER PUBLICATIONS

P. J. Burt, "Invited Address: A Gradient Pyramid Basis for Pattern–Selective Image Fusion," SID International Symposium Digest of Papers, Boston, May 17, 1992.

"VLSI Pyramid Chip for Multiresolution Image Analysis," Gooitzen S. Van Der Val and Peter J. Bert, *International Journal of Computer Vision*, 8:3, 177–189 (1992).

"The Laplacian Pyramid as a Compact Compute Code," Peter J. Bert, *IEEE Transactions on Communications*, Vol. Com–31, No. 4, Apr., 1983.

Yoshinobu Ebisawa, Improved Video–Based Eye–Gaze Detection Method, Proceedings of Instrumentation and Measurment Technology Conference, IEEE, pp. 963–966, May 1994.

*Primary Examiner*—Leo H. Boudreau
*Assistant Examiner*—Brian P. Werner
*Attorney, Agent, or Firm*—Buchanan Ingersoll, P.C.

[57] ABSTRACT

A reliable method and apparatus for illuminating and imaging eyes uses multiple light sources producing multiple images of a subject each created under illumination by different illuminators. A composite image of the subject is formed by selecting pixels based upon their gray scale values or using pyramid image processing. A composite image can be created which is free of bright spots commonly caused by reflection of illumination from eyeglasses that may be worn by a subject or for which is free of dark shadows or which is free of both bright spots and dark shadows.

36 Claims, 6 Drawing Sheets

METHOD AND APPARATUS FOR REMOVAL OF BRIGHT OR DARK SPOTS BY THE FUSION OF MULTIPLE IMAGES

FIELD OF THE INVENTION

The invention relates to the removal of bright spots or shadows from images created by a camera where the bright spots and shadows result from the type and location of illuminators.

BACKGROUND OF THE INVENTION

The phenomenon of bright spots and shadows appearing in images taken by a camera of a subject under one or more lights or other illuminators is well known. Their presence may be considered to be a mere inconvenience or as rendering an image unacceptable for its intended purpose. Consequently, professional photographers and video camera operators are acutely aware of the light sources that are present in a scene. In many situations, such as in a photography studio, it is possible to position the subject and arrange the lighting to eliminate bright spots or glare and to minimize shadows. This problem becomes more difficult in a television studio where the subject moves rather than remains still or even remains in a specific location. Even where bright spots can be eliminated by camera and lighting positions the process of positioning can be quite time consuming. In addition, if a person is required to stay at a particular location that person may appear to be nervous or otherwise uncomfortable. Hence, the control of lighting and camera positions often does not solve the problem.

Camera images are used in a variety of locations to identify a subject whose picture has been taken. These situations range from the identification of people for security or surveillance to the identification of products and product defects in automated manufacturing lines. Bright spots often occur if a person is wearing glasses or reflective clothing and if a product has a highly reflective surface or is contained in a glass or clear plastic package. The presence of a bright spot in an image may make it impossible to identify the person, product or product defect from the image. Hence, there is a need for a method and apparatus for eliminating bright spots from images.

The art has developed a number of processes for removing artifacts such as bright spots from images. These techniques range from airbrushing to digitizing the image and then applying one or more algorithms to the image. Some techniques use two or more images which are combined. Many of these prior art methods are quite time consuming taking several minutes or even hours to complete. Some prior art methods require computer hardware having large memory capacities which can be quite expensive. Thus, there is a preference for image processing that can be done rapidly using less memory and less expensive computer hardware.

There are several methods known as biometrics for recognizing or identifying an individual from personal biological characteristics. Some of these methods involve imaging of the face or eye and analyzing the facial features, retinal vascular patterns of the eye, or patterns in the iris of the eye. In recent years there has been a demand for more reliable systems to rapidly identify individuals, particularly those persons who desire access to a secured area or system. A common example of such a secured system are automated teller machines which allow authorized users to conduct banking transactions. Many of these systems are used by a wide variety of people. Very often these people demand quick as well as accurate identification. U.S. Pat. No. 5,717,512 to Chmielewski et al. discloses a compact system for rapidly obtaining images of the eye of a user of an automated teller machine. These images are then used to identify the user based upon patterns in the user's iris.

A technique for accurately identifying individuals using iris recognition is described in U.S. Pat. No. 4,641,349 to Flom et al. and in U.S. Pat. No. 5,291,560 to Daugman. The systems described in these references require clear, well-focused images of the eye. The presence of eyeglasses tends to interfere with good eye images because of reflections on the eyeglasses. Contact lenses may also cause reflections that interfere with eye imaging. However, because contact lenses have a greater curvature than eyeglasses reflections from contact lenses are smaller and less of a problem than reflections from eyeglasses.

Reflections may come from the system's own illumination. In this case, calculations show that the irradiance (illuminance for visible light) at the camera lens from the specular reflection of an illuminator from eyeglasses is on the order of 1000 times greater than the irradiance at the camera of the image of the eye caused by diffuse reflection of the illuminator. A camera viewing the eye must have a combination of lens, aperture, and exposure time that will result in a sufficiently bright image of the eye. Thus, the much brighter specular reflection of the illuminator will saturate the picture elements (pixels) of the camera's image sensor that cover the area of the specular reflection, and all information about the portion of an eye image obscured by this reflection will be lost.

It is possible to ask the subject to remove his or her eyeglasses in order to get a good image of the subject's eye. However, this is potentially annoying, and the subject may refuse to remove the glasses, or avoid using the system. Consequently, there is a need for an imaging system that can obtain useful images of the eye while minimizing the effect of bright spots, often called specular reflections, caused by the system's own illumination without requiring the subject to remove any eyeglasses or contact lenses that may be present.

Since specular reflection of illumination on eyeglasses depends on the geometric arrangement of illumination with respect to the eyeglasses and an imaging camera, one could use multiple light sources with relatively wide spacing from one another, and turn off one or more of the light sources which cause specular reflections on the eyeglasses that obscure the camera's view of the iris. Yet, these techniques will not eliminate all specularities in images of all subjects using a system because the subjects change while for practical reasons the positions of the lighting and camera must remain fixed or can be varied very little. Nevertheless, the same physical arrangement of camera and illuminators may be used as a platform for a method of image fusion for removing the negative effects of these specular reflections.

In general, image fusion involves three steps: (1) acquiring two or more images of the same scene such that good data for each point in the scene may be obtained from one of the images, (2) a method to detect good data at each point, and (3) a method to merge the data from the images into a single image. Two or more images of the same scene may be created by using different sources and angles of illumination for each image, and one approach for finding good data and fusing it into a single image is multi-resolution image processing, also called pyramid processing.

In "A VLSI Pyramid Chip for Multiresolution Image Analysis" by Van der Wal and Burt (*International Journal of*

Computer Vision, Vol. 8 No. 3, 1992, pp. 177–189), multiple types of pyramid processing of images are briefly but precisely described. In particular, the Laplacian pyramid is defined. As described in detail in "The Laplacian Pyramid as a Compact Image Code" by Burt and Adelson (*IEEE Transactions on Communications*, Vol. COM-31, No. 4, April 1983, pp. 532–540), the Laplacian pyramid represents an image as a set of bandpass components. The Laplacian pyramid representation of an image enables examination and filtering of various spatial frequency bands, and also the composition of a single image from spatial frequency components selected from multiple images.

Several United States patents show the use of the Laplacian pyramid and related multi-resolution image processing to achieve various objectives. In U.S. Pat. No. 4,661,986, for "Depth-of-focus Imaging Process Method", Adelson teaches a method of using pyramid processing to synthesize an optimally focused image from multiple images. U.S. Pat. Nos. 5,325,449 and 5,488,674, both titled "Method for Fusing Images and Apparatus Therefor", to Burt et al. teach the use of pyramid processing and directionally-sensitive spatial frequency filters to form a composite image with extended information content. "The Noise Reduction System" of Adelson et al in U.S. Pat. No. 5,526,446 uses multi-resolution image processing to filter noise from images. These methods are directed to the hardware and procedures used to process images without concern as to how the images are obtained. They tend to require expensive hardware and can be relatively slow.

SUMMARY OF THE INVENTION

We provide a method and apparatus that combines camera and lighting control with a particular image fusion technique to produce high quality images that are free of bright spots or specularities. A variation of our method can be used to remove shadows or remove both dark spots and bright spots. The images produced by our method and apparatus can be used to identify the subject present in the image using even the most demanding subject identifying methods. In a preferred embodiment our images are used to identify individuals using the face or eye images. Our method and apparatus are particularly useful for creating images that are used to identify a person from that person's iris.

First we select multiple light sources with relatively wide spacing from one another. We fuse images of the subject captured in quick succession and illuminated by different light sources. We use at least two images each comprised of pixels having a gray scale value. The images are taken or modified so that we can pair pixels one from each image such that both pixels in the pair correspond to a single point on the subject in the image. To create an image free of specular reflections we select the pixel from each pair having the lower gray scale value. Shadows can be removed by selecting the pixel having the higher gray scale value only if that value is below a threshold. The same technique can be used with three or more images by creating sets of pixels, one from each image and selecting the minimum value pixel or the maximum value pixel from each set. In yet another variation we use pyramid image processing to remove bright spots, dark spots or both bright spots or dark spots.

Our method and apparatus have particular applicability to images created by video cameras and which contain a set of raster lines. For such images we can choose only the even raster lines as our first image and only the odd raster lines of the same image as our second image. These images contain half as much data as the complete image and thus can be processed faster. Our image fusion methods can be combined with image subtraction to remove ambient lighting and can also be used with other imaging processing techniques.

Other objects and advantages of our method and apparatus will become apparent from a description of certain present preferred embodiments thereof which are shown in the drawings.

DESCRIPTION OF THE PREFERRED EMBODIMENTS

Figure 1:
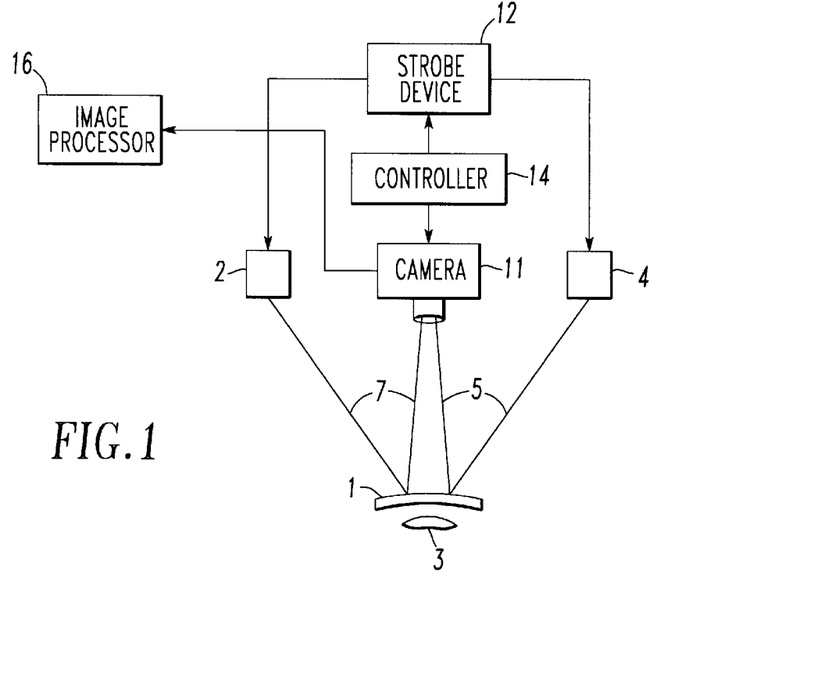
FIG. 1 is a diagram showing two light sources are used to illuminate an eye behind an eyeglass lens for imaging by a camera that is synchronized to the two light sources.

Although our method and apparatus can be used for images of any subject, they are particularly useful for obtaining images of the eye of a person wearing eyeglasses. In a preferred embodiment we use two illuminators and a video camera as illustrated by the diagram of FIG. 1. The eye 1 of a subject with eyeglass lens 3 is looking into a camera 11. The eye is illuminated by a first light source 2 and a second light source 4. The emission patterns of the light sources 2 and 4 are such that either of them generates illumination that is fairly even across the front surface of the eye 1 with sufficient intensity for the camera 11 to record a good image of the eye 1.

Instead of leaving both light sources 2 and 4 on during the time that a subject is present, the light sources 2 and 4 are pulsed or flashed in synchronization with the exposure times of the camera 11. This can be done using a strobing device 12 and an illumination controller 14 connected to the strobing device 12 and the camera 11. Both the intensity and duration of these pulses are controlled to get the correct exposure of the images of the eye 1.

Figure 2:
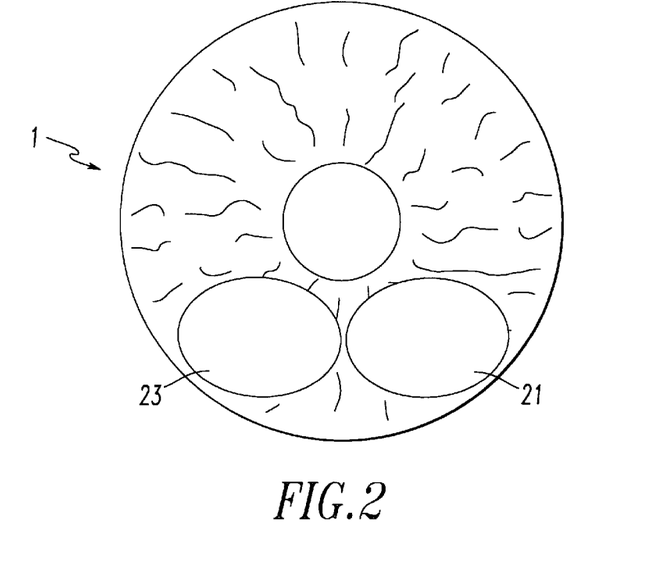
FIG. 2 is a view of an eye as seen by an imaging camera through an eyeglass lens with the view of the iris partially obscured by specular reflection of illuminating light sources.
Figure 3:
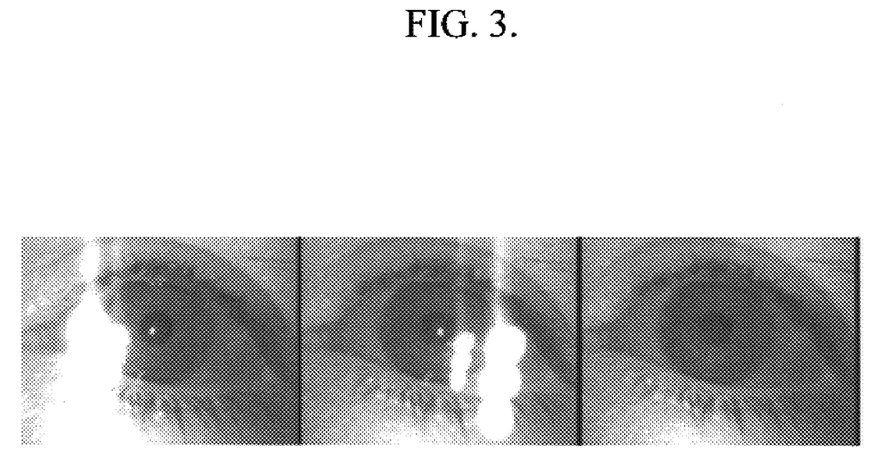
FIG. 3 shows a left-illuminated eye image, a right-illuminated image of the same eye, and a third image formed by fusion of the other two images.

At least one light path 7 from a light source 2 to the camera 11 produces a specular reflection from a first surface (front or back) of the eyeglass lens 3 and thus generates a virtual image 21 of the light source 2 that is visible to the camera 11 as seen in the camera's view illustrated in FIG. 2. Similarly, at least one light path 5 from a light source 4 to the camera 11 produces a specular reflection from the same first surface of the eyeglass lens 3 and thus generates a virtual image 23 of the light source 4 that is visible to a camera 11 as seen in the camera's view of an eye 1 illustrated in FIG. 2. Although FIG. 2 shows only one pair of virtual images 21 and 23 caused by a first surface of an eyeglass lens 3, the second surface of the lens will normally cause another pair of virtual images. These images act the same as the images caused by the first surface in all material respects. Both virtual image 21 and virtual image 23 may obscure portions of the iris of eye 1 in the view of the camera 11. Therefore, the controller 14 will turn off the first light source 2 which causes the virtual image 21, while continuing to activate the second light source 4, during exposure of a first image as shown on the left of FIG. 3. Immediately thereafter, the controller 14 will turn off the second light source 4 which causes the virtual image 23, while continuing to activate the first light source 2, during exposure of a second image as shown in the middle of FIG. 3. From these two images we form the composite image shown in the right portion of FIG. 3 using an image processor 16. That composite image is formed from the first image and the second image by choosing a pixel from corresponding locations in the first and second images at each pixel location based upon gray scale values of the pixels. This can be more easily understood by referring to FIGS. 4 and 5.

Figure 4:
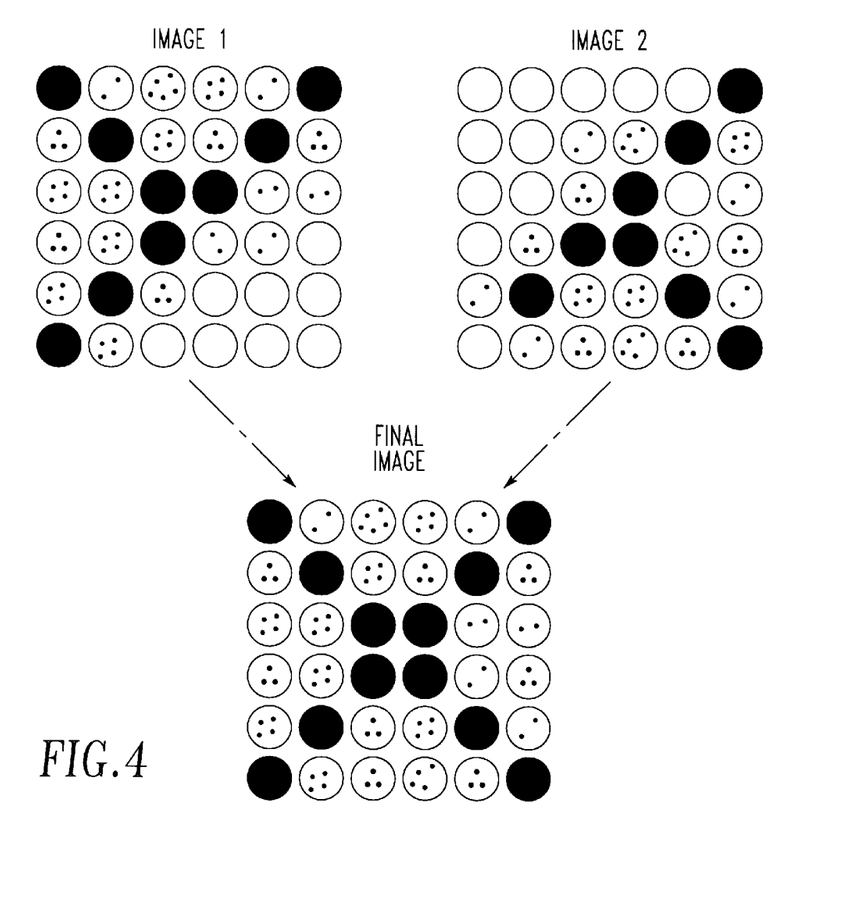
FIG. 4 is a diagram of illustrating a first present preferred embodiment of our method for fusing two images.

An image is comprised of a matrix of pixels each having a gray scale value. Depending upon the size of an image there may be hundreds or even thousands of pixels arranged in an array. Each pixel has a unique x,y coordinate position. Therefore, if there are two images of the same subject there will be one pixel in each image that corresponds to a single point on the subject. If the two images were taken under different lighting conditions the gray scale value of the pixel in the first image that corresponds to a selected point on the subject may be different from the gray scale value of the pixel in the second image that corresponds to the same point. In FIG. 4 there are three images formed from thirty six pixels arranged in a six by six array. It should be understood that the images that are used and created will be substantially larger than the six by six images presented here to illustrate our concept. Indeed, we prefer to use a camera that produces an image which is 640 pixels by 480 pixels. Image 1 and Image 2 were taken under different lighting conditions which created a bright spot in each image. The bright spot is represented by the open circles. The remaining circles are shaded to indicate three gray scale values represented by filled circles, circles containing several dots and circles containing only three dots. The bright spot in each image has obscured a portion of the subject. Therefore, we select a pixel from either Image 1 or Image 2 for each pixel position, or x,y coordinate position, in the six by six array to form the Final Image in FIG. 4. That Final Image presents a clear image of the subject which is the letter X.

Figure 5:
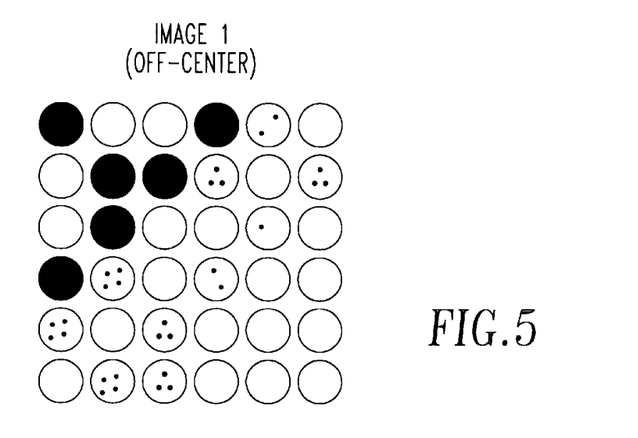
FIG. 5 is a diagram of an off center image.

In Image 1 and Image 2 the same pixels location in both images corresponded to the same unique point on the subject. It may happen that two images are presented where this is not true. One example of this occurrence is illustrated by FIG. 5. That image shows much of the same content as Image 1 in FIG. 4. Should one image be off center relative to the other image, it is necessary to preprocess one or both images so that a proper pairing can be made. There are several techniques that are well known to those skilled in the art which will accomplish this preprocessing. In the discussion that follows we assume that there has been minimal movement of the subject during the time from capture of the first image to capture of the second image, or that some preprocessing has occurred, to ensure that each physical point on the subject appears at the same (x,y) position in both images.

Normal video images are made up of lines of pixels called raster lines. These raster lines can be consecutively numbered and grouped into two fields. One field contains the odd raster lines and the second field contains the even raster lines. If a first illuminator and a second illuminator are alternately illuminated at the same frame rate as the video camera, then one field for a single image will have been created with the first illuminator activated and the other field for that image will have been created with the second illuminator activated. Consequently, if video images are available we can select the even field as our first image and the odd field as our second image or vice versa. If this is done we assume that adjacent pairs of pixels in the video image, one pixels from an odd raster line and the other pixel from an even raster line, correspond to a single unique point on the subject.

One can consider the two initial images as image A and image B with the final composite image being image C. If the first image has pixel values A(x,y) where x and y are coordinates of a two-dimensional, orthogonal coordinate system for specifying the position of pixels in the view of the camera, and the second image has pixel values B(x,y), then the composite image created in accordance with our method has pixel values C(x,y)=MIN(A(x,y), B(x,y)) where MIN is the minimum function that selects the least of its two parameters. We have observed that most, if not all, pixels which represent a specularity have a gray scale value 255. By selecting a minimum gray scale we effectively remove the specularities from the image. Shadows can be removed by selecting pixels having a maximum gray scale value. However, to avoid selection of pixels that represent specularities or saturation we select the maximum gray scale value that is below a threshold gray scale value such as 255.

Our method also overcomes any blooming that may occur. Calculations show that the irradiance (illuminance for visible light) at the camera lens from the specular reflection of an illuminator from eyeglasses is on the order of 1000 times greater than the irradiance at the camera of the image of the eye caused by diffuse reflection of the illuminator. A camera viewing the eye must have a combination of lens, aperture, and exposure time that will result in a sufficiently bright image of the eye. Thus, the much brighter specular reflection of the illuminator will saturate the picture elements (pixels) of the camera's image sensor that cover the area of the specular reflection, and all information about the portion of an eye image obscured by this reflection will be lost. Furthermore, the values of pixels surrounding the area of the specular reflection may be corrupted by the saturated pixels in a phenomenon called "blooming". This occurs because the pixels of charge-coupled devices (CCD's), the most common electronic imagers, are not well isolated from one another. As long as the two light sources 2 and 4 are sufficiently separated so that the virtual image 23 and its associated blooming does not overlap virtual image 21 and its associated blooming, every portion of the subject is clearly visible in at least one of the first image or the second image. Hence, in one or both of the left image and center image of FIG. 3 every portion of a person's iris can be clearly seen. Therefore, the rightmost composite image of FIG. 3 contains a good view of the entire iris.

The light sources 2 and 4 may be implemented with one or more high-power light-emitting diodes (such as the OD-669 IR LED array manufactured by Opto-Diode Corporation), a laser diode fed through an optical fiber, a laser fitted with a diverging lens, an incandescent lamp, or any other source that produces sufficient power with appropriate emission pattern in the appropriate spectral band. The light sources may produce visible light or non-visible light such as infrared.

Although FIG. 1 shows two light sources 2 and 4 arranged horizontally, two or more light sources may be arranged horizontally, vertically, radially, or in any other geometry so long as the spacing of the light sources is sufficient for the virtual images of the sources reflected from an eyeglass lens in the camera's view of an eye to be separated far enough so that the illumination controller can use one or more of the sources to sufficiently illuminate each portion of the iris without an obscuring specular reflection or blooming in at least one of the multiple images to be used to form the composite output image.

Figure 6:
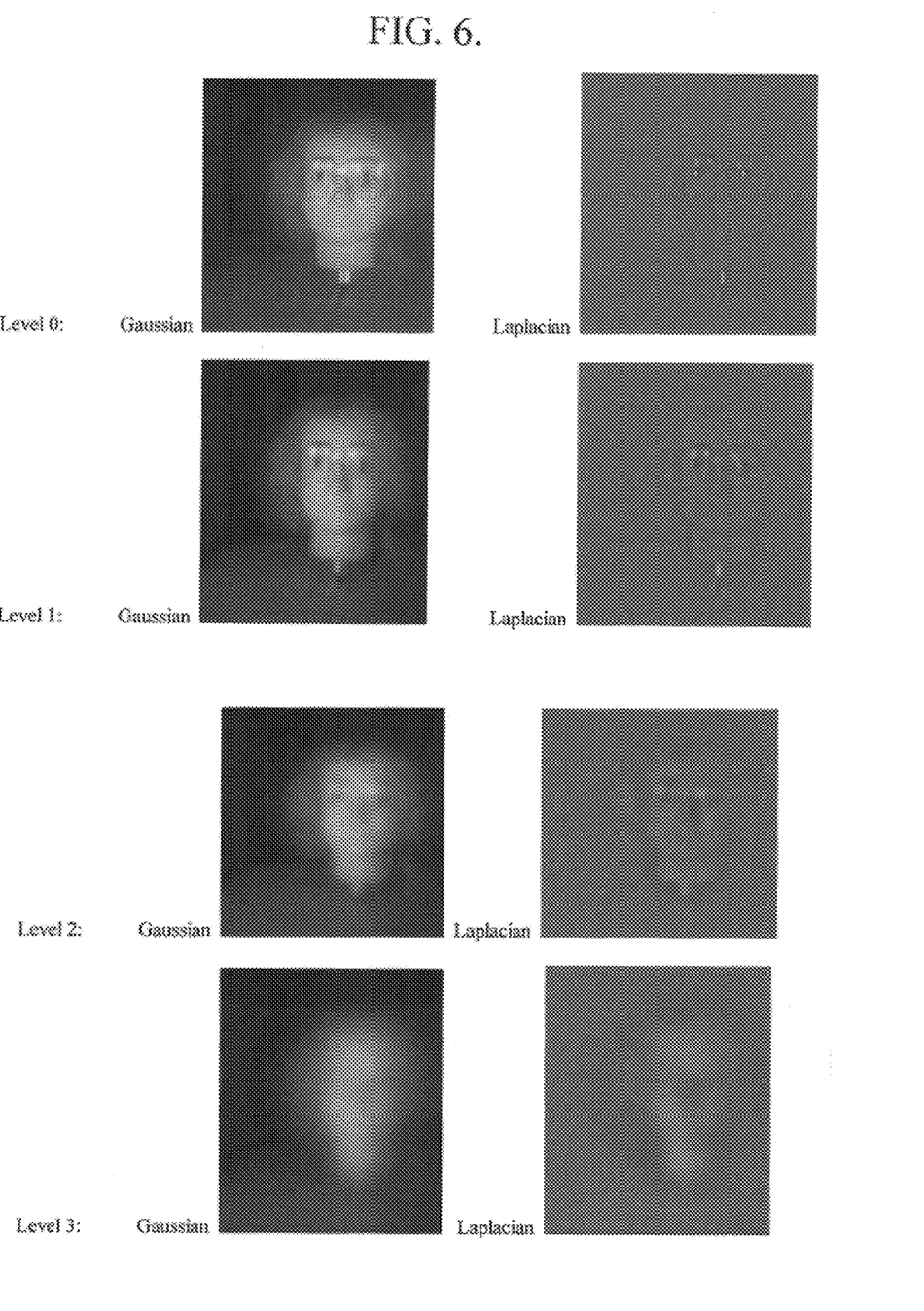
FIG. 6 is a series of images created in a Laplacian pyramid.

A second preferred embodiment of our method may use any of the arrangements of the first embodiment such as the one shown in FIG. 1, but the image processing uses Laplacian pyramid computations of both the first and second input images. This variation is preferred when trying to find the eyes in a wider view of a subject's face. The calculation of a Laplacian pyramid of a sample image is illustrated in FIG. 6.

Figure 8:
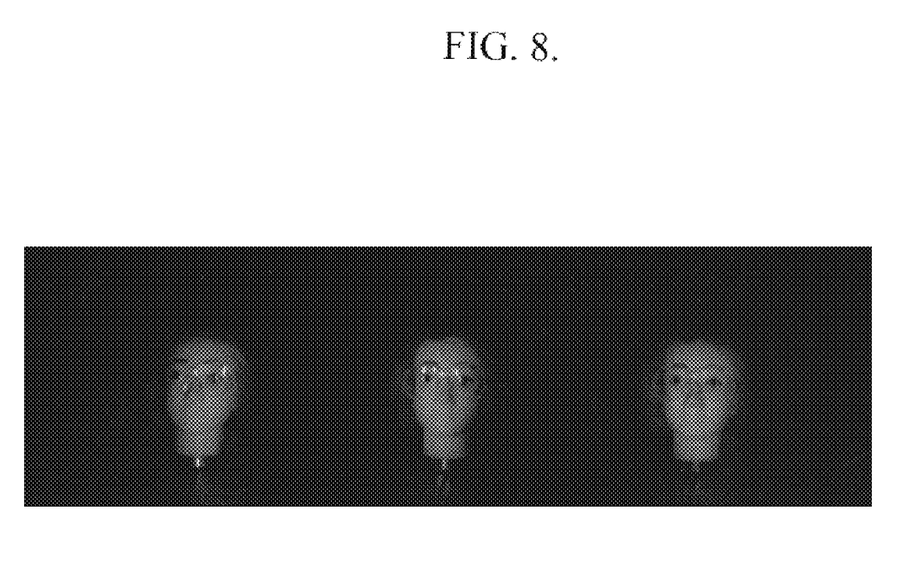
FIG. 8 shows a right-illuminated facial image of a mannequin, a left-illuminated facial image of the same mannequin, and a third image formed by fusion of the other two images using Laplacian pyramids.

The process begins with an original image which could be either the left or center image in FIG. 8. The original image in FIG. 6 is the middle image of FIG. 8. The original image is called the Level 0 Gaussian image. The column of images on the left is the Gaussian pyramid of the original image which is composed of successively lower spatial frequency approximations of the original image. From top to bottom, these levels are identified as Level 0, Level 1, Level 2 and Level 3. It should be understood that additional levels may also be created. The column of images on the right is the Laplacian pyramid of the original image which is composed of images representing the differences between successive levels of the Gaussian pyramid. From top to bottom, these are similarly called the Level 0, Level 1, Level 2 and Level 3 Laplacian images. Thus, the Laplacian image at Level 0 is the Level 0 Gaussian image minus the Level 1 Gaussian image. The Level 3 Laplacian image is the Level 3 Gaussian image minus the Level 4 Gaussian image which is not shown in FIG. 6. In effect, these are successively lower spatial frequency passband components of the original image. Furthermore, the original image may be recovered from the Laplacian pyramid and the highest level (lowest frequency approximation) of the Gaussian pyramid by reversing the difference operations to perform an inverse Laplacian transform. The mathematical details of this pyramid processing are given in "A VLSI Pyramid Chip for Multi-resolution Image Analysis" by Van der Wal and Burt (*International Journal of Computer Vision*, Vol. 8 No. 3, 1992, pp 177–189) where the required calculation of the Laplacian pyramid is called the RE (for reduce-expand) Laplacian.

Figure 7:
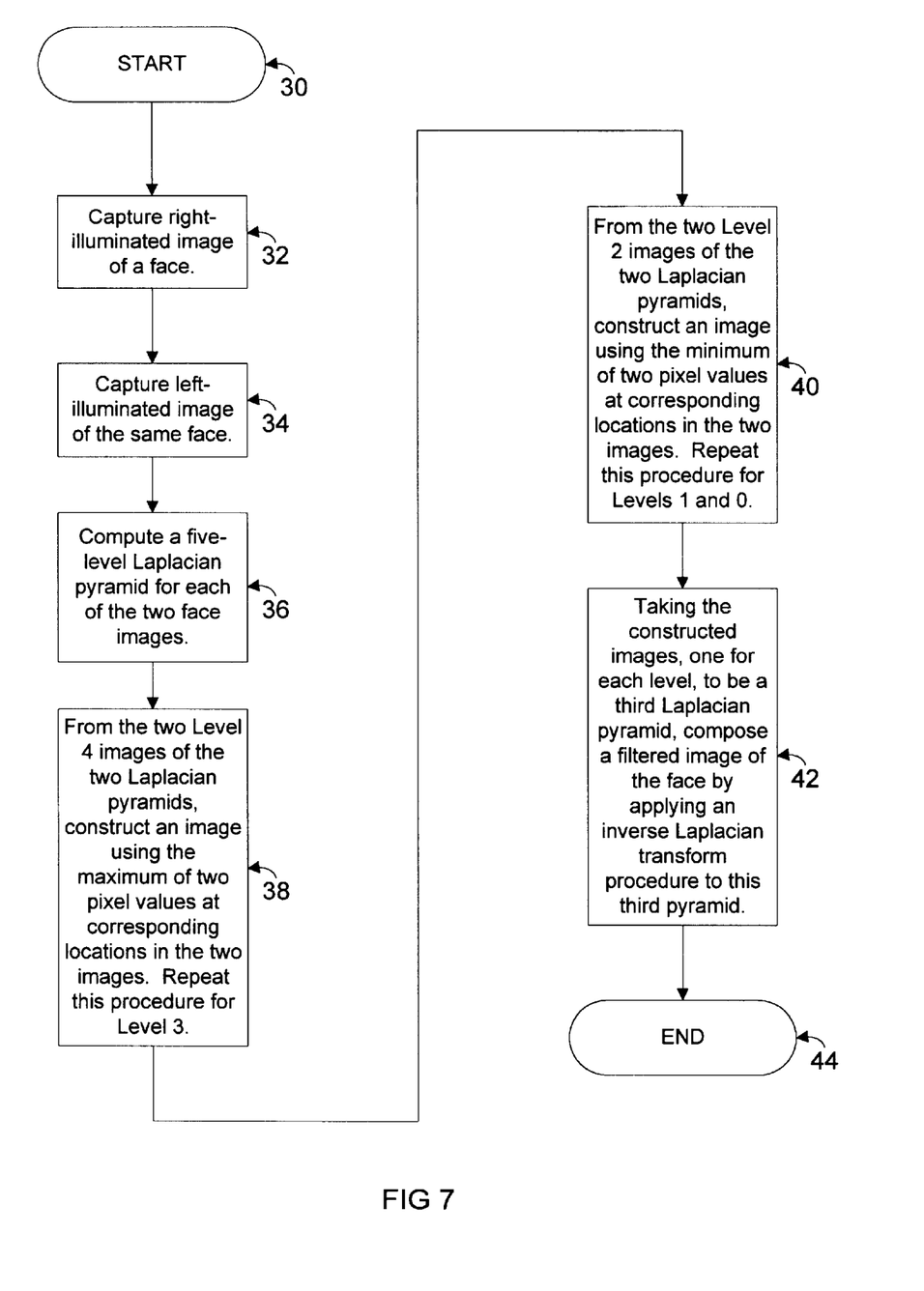
FIG. 7 is a flowchart of a second present preferred method of removing bright spots by the fusion of two images using Laplacian pyramids.

Using these pyramid processes, the second preferred embodiment proceeds according to the flowchart shown in FIG. 7. After starting at step 30, the system captures a right-illuminated image of a subject's face (step 32) as shown in the leftmost image of FIG. 8. Then the system captures a left-illuminated image of a subject's face (step 34) as shown in the middle image of FIG. 8. The system computes five-level Laplacian pyramids for both of these images in step 36. Only four levels of Laplacian images for the middle image of FIG. 8 are shown in FIG. 6.

In step 38, we construct composite images from the higher levels (3 and 4) of the two Laplacian pyramids computed in Step 36. Specifically, if the image at a particular level of the Laplacian pyramid derived from the left-illuminated image has pixel values $L(x,y)$ where x and y are coordinates of a two-dimensional, orthogonal coordinate system for specifying the position of pixels in the view of the camera, and the image at the same level of the Laplacian pyramid derived from the right-illuminated image has pixel values $R(x,y)$, then the composite image has pixel values $C(x,y)=MAX(L(x,y), R(x,y))$ where MAX is the maximum function that selects the larger of its two parameters. As in the first preferred embodiment, we assume that there has been minimal movement of the subject during the time from capture of the left-illuminated image to capture of the right-illuminated image, or that some preprocessing has occurred, to ensure that each physical point on the subject appears at the same (x,y) position in the left-illuminated and right-illuminated images.

In step 40, we construct composite images from the lower levels (0, 1, and 2) of the two Laplacian pyramids computed in Step 36. Specifically, if the image at a particular level of the Laplacian pyramid derived from the left-illuminated image has pixel values $L(x,y)$ where x and y are coordinates of a two-dimensional, orthogonal coordinate system for specifying the position of pixels in the view of the camera, and the image at the same level of the Laplacian pyramid derived from the right-illuminated image has pixel values $R(x,y)$, then the composite image has pixel values $C(x,y)=MIN(L(x,y), R(x,y))$ where MIN is the minimum function that selects the least of its two parameters. As in the first preferred embodiment, we assume that there has been minimal movement of the subject during the time from capture of the left-illuminated image to capture of the right-illuminated image, or that some preprocessing has occurred, to ensure that each physical point on the subject appears at the same (x,y) position in the left-illuminated and right-illuminated images.

In step 42, we take the composite images formed at each level in steps 38 and 40 to be a third Laplacian pyramid. On this third pyramid, we perform an inverse Laplacian transform to get a filtered image as illustrated in the rightmost image of FIG. 8. The process is now complete (step 44).

It is easy to see in FIG. 8 that the specular reflections of illumination on the eyeglasses that are visible in the two input images (left and middle) have been removed in the filtered output image (right). This is achieved in the calculations of step 40, which are very similar to the simple calculations of the first preferred embodiment.

It may also be seen in FIG. 8 that the dark shadows on the edge of the face that is away from the illuminating light source in each of the input images (left and middle) have been removed in the filtered output image (right). This is achieved in the calculations of step 38, which are different than the simple calculations of the first preferred embodiment.

The overall effect of this second preferred embodiment is to remove small bright spots, usually caused by specular reflections, without including larger dark regions that may occur in one or more of the input views. As in the first preferred embodiment, more than two input images may be used.

Several variations of the second preferred embodiment may be implemented. The Laplacian pyramids of the input images may have any number of levels appropriate to the resolution of the input images. Those skilled in the art will recognize that the first embodiment of our method shown in FIGS. 3, 4 and 5 is an inverse Laplacian transform of a degenerate Laplacian pyramid consisting of a single base Gaussian image. The grouping of the higher level composite images for maximum selection and the lower level composite images for minimum selection may be adjusted to filter out larger or smaller bright spots by including more or fewer levels in the lower level group for minimum selection. The roles of the maximum and minimum functions may be reversed to filter out smaller dark spots without including larger bright regions that may occur in one or more of the input images. We may also replace minimum with maximum in the first preferred embodiment in order to remove dark regions, usually caused by shadows, in one or more of the input images.

In yet another embodiment we create the initial images, previously called Image 1 and Image 2, by image subtraction. In this embodiment we capture one image with only the first illuminator on, a second image with only the second illuminator on and a third image with both illuminators off. We then create Image 1 by subtraction the third image from the first image and create Image 2 by subtracting the third image from the second image. This subtraction has the effect of removing ambient illumination. We prefer to implement our method using a video camera. In a present preferred implementation we have a first video image in which one field has the first illuminator on and the second field has both illuminators off. In a second image both fields have the second illuminator on. We then subtract field two from field one in the first image to create Image 1. Field two from the first image (both illuminators off) is subtracted from either of the fields of the second image to form Image 2. We have implemented this procedure using a camera which creates a 640 pixels by 480 pixels image. Hence, the resulting images after subtraction are 640 pixels by 240 pixels or half size. Yet, sometimes we may need an illuminated, full size image in order to locate a corneal reflection that would tell us the position of an eye in the image. We will have that full size, fully illuminated image by using this illumination scheme.

We have described the present invention as used for imaging eyes or faces. However, there are other applications for this invention in which an image is taken of an object that is behind a lens or other light transmissive curved structure. For example, this method and apparatus could be used to obtain images of products packaged in light transmissive packaging such as glass jars or blister packages. Such images could be used for quality control or product identification purposes.

The light transmissive structure is not limited to clear materials. That structure may allow passage of limited wavelengths of light which could be visible or invisible to the human eye. A common example of such a structure are the plastics used in sunglasses.

Although we have shown certain present preferred embodiments of our invention, it should be distinctly understood that the invention is not limited thereto, but may be variously embodied within the scope of the following claims.

We claim:

1. A method for creating an image of at least a portion of a head of a person who is wearing eyeglasses or contact lens and who is positioned at a subject location which image is free of specularities comprising:

a. positioning a first illuminator and at least one additional illuminator at a selected distance from the subject location and spaced apart from one another;
   b. capturing a first image of at least a portion of a head of a person who is wearing eyeglasses or contact lens while the person's head is illuminated by the first illuminator and not illuminated by the at least one additional illuminator wherein the first image is comprised of a set of pixels each pixel corresponding to a specific location relative to the person's head and having a gray scale value;
   c. capturing at least one additional image of at least a portion of a head of a person who is wearing eyeglasses or contact lens while the person's head is illuminated by the at least one additional illuminator and not illuminated by the first illuminator; wherein the second image is comprised of a set of pixels each pixel corresponding to a specific location relative to the person's head and having a gray scale value;
   d. creating sets of pixels such that each set contains a pixel from the first image and a pixel from each additional image and all pixels in each set correspond to a same location relative to the subject; and
   e. constructing an image of the subject that is free of specularities by selecting one pixel from each set of pixels by choosing that pixel which has a minimum gray scale value.

2. The method of claim 1 wherein there is only one additional illuminator and only one additional image.

3. The method of claim 1 wherein the illuminators emit infrared light.

4. The method of claim 1 wherein at least one of the illuminators is an illuminator selected from the group consisting of light-emitting diodes, laser diodes, lasers fitted with a diverging lens, and an incandescent lamp.

5. The method of claim 1 also comprising the step of using the image of the at least a portion of a head of a person that is free of specularities to identify the person.

6. The method of claim 5 wherein the person is identified using a biometric identification method.

7. The method of claim 6 wherein the biometric identification method is iris identification.

8. The method of claim 1 wherein the first image is captured by:

a. capturing a first preliminary video image of the at least a portion of a head of a person which contains a field created while the at least a portion of a head of a person is illuminated by the first illuminator and not illuminated by the at least one additional illuminator and a second field which was created while the at least a portion of a head of a person was not illuminated by any illuminator wherein the first image is comprised of a set of pixels each pixel corresponding to a specific location relative to the at least a portion of a head of a person and having a gray scale value; and
   b. forming the first image by subtraction of the second field from the first field.

9. The method of claim 8 wherein the at least one additional image is captured by:

a. capturing a second preliminary video image of the subject which contains two fields created while the at least a portion of a head of a person is illuminated by the at least one additional illuminator and not illuminated by the first illuminator and a second field which was created while the at least a portion of a head of a person was not illuminated by the first illuminator and wherein the second image is comprised of a set of pixels each pixel corresponding to a specific location relative to the at least a portion of a head of a person and having a gray scale value; and
   b. forming the second image by either subtraction from the first field of the second preliminary image of the second field of the first preliminary image or by subtraction from the second field of the second preliminary image of the second field of the first preliminary image.

10. A method for creating an image of a subject positioned at a subject location which image is free of specularities comprising:

a. positioning a first illuminator and at least one additional illuminator at a selected distance from the subject location and spaced apart from one another;

b. capturing a first image of the subject while the subject is illuminated by he first illuminator and not illuminated by the at least one additional illuminator wherein the first image is comprised of a set of pixels each pixel corresponding to a specific location relative to the subject and having a gray scale value;

c. capturing at least one additional image of the subject while the subject is illuminated by the at least one additional illuminator and not illuminated by the first illuminator; wherein the second image is comprised of a set of pixels each pixel corresponding to a specific location relative to the subject and having a gray scale value;

d. creating sets of pixels such that each set contains a pixel from the first image and a pixel from each additional image and all pixels in each set correspond to a same location relative to the subject;

e. constructing an image of the subject that is free of specularities by selecting one pixel from each set of pixels by choosing that pixel which has a minimum gray scale value;

f. capturing a third image of the subject wherein the third image is comprised of a set of pixels each pixel corresponding to a specific location relative to the subject and having a gray scale value; and g. including a pixel from the third image in at least some of the sets of pixels.

11. A method for creating an image of a subject that is located in a package at least a portion of which package is light transmissive which image is free of specularities comprising:

a. positioning a first illuminator and at least one additional illuminator at a selected distance from the subject location and spaced apart from one another;

b. capturing a first image of the subject while the subject is illuminated by the first illuminator and not illuminated by the at least one additional illuminator wherein the first image is comprised of a set of pixels each pixel corresponding to a specific location relative to the subject and having a gray scale value;

c. capturing at least one additional image of the subject while the subject is illuminated by the at least one additional illuminator and not illuminated by the first illuminator; wherein the second image is comprised of a set of pixels each pixel corresponding to a specific location relative to the subject and having a gray scale value;

d. creating sets of pixels such that each set contains a pixel from the first image and a pixel from each additional image and all pixels in each set correspond to a same location relative to the subject; and e. constructing an image of the subject that is free of specularities by selecting one pixel from each set of pixels by choosing that pixel which has a minimum gray scale value.

12. method of claim 11 wherein the illuminators emit infrared light.

13. The method of claim 11 wherein at least one of the illuminators is an illuminator selected from the group consisting of light-emitting diodes, laser diodes, lasers fitted with a diverging lens, and an incandescent lamp.

14. The method of claim 11 also comprising the step of using the image of the subject that is free of specularities to identify the subject.

15. The method of claim 11 wherein the first image is captured by:

a. capturing a first preliminary video image of the subject which contains a field created while the subject is illuminated by the first illuminator and not illuminated by the at least one additional illuminator and a second field which was created while the subject was not illuminated by any illuminator wherein the first image is comprised of a set of pixels each pixel corresponding to a specific location relative to the subject and having a gray scale value; and b. forming the first image by subtraction of the second field from the first field.

16. The method of claim 15 wherein the at least one additional image is captured by:

a. capturing a second preliminary video image of the subject which contains two fields created while the subject is illuminated by the at least one additional illuminator and not illuminated by the first illuminator and a second field which was created while the subject was not illuminated by the first illuminator and wherein the second image is comprised of a set of pixels each pixel corresponding to a specific location relative to the subject and having a gray scale value; and b. forming the second image by either subtraction from the first field of the second preliminary image the second field of the first preliminary image or by subtraction from the second field of the second preliminary image the second field of the first preliminary image.

17. A method for creating a shadow free image of a subject positioned at a subject location comprising:

a. positioning a first illuminator and at least one additional illuminator at a selected distance from the subject location and spaced apart from one another;

b. capturing a first image of the subject while the subject is illuminated by the first illuminator and not illuminated by the at least one additional illuminator wherein the first image is comprised of a set of pixels each pixel corresponding to a specific location relative to the subject and having a gray scale value;

c. capturing at least one additional image of the subject while the subject is illuminated by the at least one additional illuminator and not illuminated by the first illuminator; wherein the second image is comprised of a set of pixels each pixel corresponding to a specific location relative to the subject and having a gray scale value;

d. creating sets of pixels such that each set contains a pixel from the first image and a pixel from each additional image and all pixels in each set correspond to a same location relative to the subject; and e. constructing an image of the subject by selecting one pixel from each set of pixels by choosing that pixel which has a maximum gray scale value that is less than a threshold gray scale value.

18. The method of claim 17 wherein the threshold gray scale value is 255.

19. The method of claim 17 wherein there is only one additional illuminator and only one additional image.

20. The method of claim 17 wherein the subject is at least a portion of a head of a person who is wearing eyeglasses or contact lenses.

21. The method of claim 17 wherein the subject is located in a package at least a portion of which is light transmissive.

22. The method of claim 17 wherein the illuminators emit infrared light.

23. The method of claim 17 wherein at least one of the illuminators is an illuminator selected from the group consisting of light-emitting diodes, laser diodes, lasers fitted with a diverging lens, and an incandescent lamp.

24. A method for creating an image of a subject positioned at a subject location comprised of:
   a. positioning a first illuminator and at least one additional illuminator at a selected distance from the subject location and spaced apart from one another;
   b. capturing a first image of the subject while the subject is illuminated by the first illuminator and not illuminated by the at least one additional illuminator wherein the first image is comprised of a set of pixels each pixel corresponding to a specific location relative to the subject and having a gray scale value;
   c. capturing at least one additional image of the subject while the subject is illuminated by the at least one additional illuminator and not illuminated by the first illuminator; wherein the second image is comprised of a set of pixels each pixel corresponding to a specific location relative to the subject and having a gray scale value;
   d. computing a Laplacian pyramid for each image;
   e. selecting a first particular level of the Laplacian pyramids computed for each image such that a same level is selected for each image;
   f. creating sets of pixels such that each set contains a pixel from the selected level of the Laplacian pyramid for each of the first image and each additional image and all pixels in each set correspond to a same location relative to the subject;
   g. identifing a pixel in each set which has a maximum value and identifying the image from which each selected pixels was derived; and
   h. constructing a first composite image of the subject by selecting one pixel from one of the first image and each additional image that corresponds to each pixel identified in step g.

25. The method of claim 24 wherein there is only one additional illuminator and only one additional image.

26. The method of claim 24 also comprising:
   a. selecting a second particular level of the Laplacian pyramids computed for each image such that a same level is selected for each image and the second particular level selected is adjacent to the first selected level;
   b. creating sets of pixels such that each set contains a pixel from the second selected level of the Laplacian pyramid for each of the first image and each additional image and all pixels in each set correspond to a same location relative to the subject;
   c. identifying a pixel in each set which has a minimum value and identifying the image from which each selected pixels was derived; and
   d. constructing a second composite image of the subject by selecting one pixel from one of the first image and each additional image that corresponds to each pixel identified in step c.

27. The method of claim 26 also comprising combining the first composite image and the second composite image to form a combined composite image.

28. The method of claim 26 also comprising:
   a. selecting at least one additional particular level of the Laplacian pyramids computed for each image such that a same level is selected for each;
   b. creating sets of pixels for each selected additional particular level such that each set contains a pixel from the additional particular selected level of the Laplacian pyramid for each of the first image and each additional image and all pixels in each set correspond to a same location relative to the subject;
   c. identifying a pixel in each set which has a minimum value and identifying the image from which each selected pixels was derived; and
   d. constructing an additional composite image of the subject for each additional selected level by selecting one pixel from one of the first image and each additional image that corresponds to each pixel identified in step c.

29. The method of claim 28 also comprising:
   a. creating a constructed Laplacian pyramid which contains the first composite image, the second composite image and at least one additional composite images; and
   b. constructing an image of the subject by applying an inverse Laplacian transform procedure to the created Laplacian pyramid.

30. The method of claim 26 also comprising:
   a. selecting at least one additional particular level of the Laplacian pyramids computed for each image such that a same level is selected for each;
   b. creating sets of pixels for each selected additional particular level such that each set contains a pixel from the additional particular selected level of the Laplacian pyramid for each of the first image and each additional image and all pixels in each set correspond to a same location relative to the subject;
   c. identifying a pixel in each set which has a maximum value and identifying the image from which each selected pixels was derived; and
   d. constructing an additional composite image of the subject for each additional selected level by selecting one pixel from one of the first image and each additional image that corresponds to each pixel identified in step c.

31. The method of claim 30 also comprising:
   a. creating a constructed Laplacian pyramid which contains the first composite image, the second composite image and at least one additional composite images; and
   b. constructing an image of the subject by applying an inverse Laplacian transform procedure to the created Laplacian pyramid.

32. A method for creating an image of a subject positioned at a subject location comprised of:
   a. positioning a first illuminator and a at least one additional illuminator at a selected distance from the subject location and spaced apart from one another;
   b. capturing a first image of the subject while the subject is illuminated by the first illuminator and not illuminated by the at least one additional illuminator wherein the first image is comprised of a set of pixels each pixel corresponding to a specific location relative to the subject and having a gray scale value;
   c. capturing at least one additional image of the subject while the subject is illuminated by the at least one additional illuminator and not illuminated by the first illuminator; wherein the second image is comprised of a set of pixels each pixel corresponding to a specific location relative to the subject and having a gray scale value;

d. computing a Laplacian pyramid for each image;

e. selecting a first particular level of the Laplacian pyramids computed for each image such that a same level is selected for each image;

f. creating sets of pixels such that each set contains a pixel from the selected level of the Laplacian pyramid for each of the first image and each additional image and all pixels in each set correspond to a same location relative to the subject;

g. identifying a pixel in each set which has a minimum value and identifying the image from which each selected pixels was derived; and h. constructing a first composite image of the subject by selecting one pixel from one of the first image and each additional image that corresponds to each pixel identified in step g.

33. The method of claim 32 wherein there is only one additional illuminator and only one additional image.

34. An apparatus for creating an image of a subject positioned at a subject location which image is free of specularities or shadows comprising:

a. a camera for taking an image of a subject located at a subject location;

b. a first illuminator and at least one additional illuminator at a selected distance from the subject location and spaced apart from one another;

c. a controller attached to the camera and the illuminators for turning on a selected illuminator whenever the camera captures an image of the subject; and d. an image processor connected to the camera for receiving a first image of the subject taken when the first illuminator is illuminated and the at least one additional illuminator is not illuminated and receiving at least one additional image of the subject taken when the first illuminator is not illuminated and the at least one additional illuminator is illuminated and combining the first image and at least one additional image to produce a composite image of the subject wherein the images are each comprised of a set of pixels each pixel corresponding to a specific location relative to the subject and having a gray scale value and wherein the image processor contains a program for combining the first and second images which program constructs a Laplacian pyramid for each image and uses at least some of levels of the Laplacian pyramids to form a composite image of the subject.

35. The apparatus of claim 34 wherein there is only one additional illuminator and only one additional image.

36. An apparatus for creating an image of a subject positioned at a subject location which image is free of specularities or shadows comprising:

a. a camera for taking an image of a subject located at a subject location;

b. a first illuminator and at least one additional illuminator at a selected distance from the subject location and spaced apart from one another;

c. a controller attached to the camera and the illuminators for turning on a selected illuminator whenever the camera captures an image of the subject; and d. an image processor connected to the camera for receiving a first image of the subject taken when the first illuminator is illuminated and the at least one additional illuminator is not illuminated and receiving at least one additional image of the subject taken when the first illuminator is not illuminated and the at least one additional illuminator is illuminated and combining the first image and at least one additional image to produce a composite image of the subject wherein the images are each comprised of a set of pixels each pixel corresponding to a specific location relative to the subject and having a gray scale value and wherein the image processor contains a program for combining the first and second images by:

a. creating sets of pixels such that each set contains a pixel from the first image and a pixel from each additional image and all pixels in each set correspond to a same location relative to the subject; and b. creating a constructed image of the subject by selecting one pixel from each set of pixels by choosing that pixel which has a maximum gray scale value that is less than a threshold gray scale value.

* * * * *

UNITED STATES PATENT AND TRADEMARK OFFICE
CERTIFICATE OF CORRECTION

PATENT NO. : 6,088,470
DATED : July 11, 2000
INVENTOR(S) : THEODORE A. CAMUS, MARCUS SALGANICOFF, THOMAS A. CHMIELEWSKI, JR., KEITH JAMES HANNA It is certified that error appears in the above-indentified patent and that said Letters Patent is hereby corrected as shown below:

Column 11, line 5, claim 10, change "he" to --the--.

Signed and Sealed this

Twenty-second Day of May, 2001

Attest:

NICHOLAS P. GODICI

Attesting Officer

Acting Director of the United States Patent and Trademark Office